(12) United States Patent  (10) Patent No.: US 9,044,148 B2
Michelson et al.  (45) Date of Patent: Jun. 2, 2015

(54) METHOD AND A SYSTEM FOR CARDIAC MONITORING

(71) Applicants: George Michelson, Glenview, IL (US); Melissa Petrucci, Wauconda, IL (US)

(72) Inventors: George Michelson, Glenview, IL (US); Melissa Petrucci, Wauconda, IL (US)

(73) Assignee: LIFEWATCH TECHNOLOGIES LTD., Rehovot (IL)

( * ) Notice: Subject to any disclaimer, the term of this patent is extended or adjusted under 35 U.S.C. 154(b) by 0 days.

(21) Appl. No.: 13/924,658

(22) Filed: Jun. 24, 2013

(65) Prior Publication Data

US 2014/0005559 A1  Jan. 2, 2014

Related U.S. Application Data

(63) Continuation of application No. 12/760,569, filed on Apr. 15, 2010, now Pat. No. 8,473,039.

(51) Int. Cl.
*A61B 5/04* (2006.01)
*A61B 5/024* (2006.01)
*G06Q 50/22* (2012.01)
*G06Q 99/00* (2006.01)

(52) U.S. Cl.
CPC ............ *A61B 5/02405* (2013.01); *G06Q 50/22* (2013.01); *G06Q 99/00* (2013.01)

(58) Field of Classification Search
None
See application file for complete search history.

(56) References Cited

U.S. PATENT DOCUMENTS

| | | | | |
|---|---|---|---|---|
| 5,362,069 | A * | 11/1994 | Hall-Tipping | 463/7 |
| 5,500,008 | A * | 3/1996 | Fain | 607/5 |
| 5,882,352 | A * | 3/1999 | Duncan et al. | 607/4 |
| 6,272,377 | B1 * | 8/2001 | Sweeney et al. | 600/515 |
| 6,480,734 | B1 * | 11/2002 | Zhang et al. | 600/518 |
| 6,537,228 | B1 * | 3/2003 | Lambert | 600/506 |
| 7,184,834 | B1 * | 2/2007 | Levine | 607/9 |
| 7,403,813 | B1 * | 7/2008 | Farazi et al. | 600/515 |
| 8,112,149 | B2 * | 2/2012 | Sholder | 600/516 |
| 2009/0299205 | A1 * | 12/2009 | Chow | 600/518 |
| 2010/0114597 | A1 * | 5/2010 | Shreiber et al. | 705/2 |
| 2011/0201945 | A1 * | 8/2011 | Li et al. | 600/484 |

* cited by examiner

*Primary Examiner* — Brian T Gedeon
(74) *Attorney, Agent, or Firm* — Oren Reches

(57) ABSTRACT

A method for monitoring a heart of a patient, the includes receiving signals indicative of cardiac activity of the patient during a monitoring period; and
processing the signals and providing monitoring results in response to a result of the processing; wherein the monitoring results comprise information indicative of: (a) the heart rate of the patient during the monitoring period; (b) at least one first time period in which the heart rate of the patient exceeds a first threshold; and (c) at least one second time period in which the heart rate of the patient exceeds both the first threshold and a second threshold.

17 Claims, 10 Drawing Sheets

510 receiving signals indicative of cardiac activity of the patient during a monitoring period 511 receiving information from other sensors/detectors/external systems 520 processing the signals 530 providing monitoring results in response to a result of the processing, wherein the monitoring results include information indicative of: (a) the heart rate of the patient during the monitoring period; (b) at least one first time period in which the heart rate of the patient exceeded a first threshold; and (c) at least one second time period in which the heart rate of the patient exceeded both the first threshold and a second threshold 540 issuing an alert when at least one of the first and the second thresholds was exceeded for a predetermined minimum duration 541 wirelessly transmitting the alert to a remote control center over a cellular telephony network 550 storing a heart rate history of heart rates detected during the monitoring period, 551 replacing stored information with newer detected information, wherein the replacing is responsive to priority levels that are associated with the first and the second thresholds 560 receiving wireless instructions over a wireless network connection, and modifying at least one of the first and the second thresholds in response to the wireless instructions

*FIG. 4A*

520 processing the signals 521 processing the signals to detect heart beating pauses 522 determining when the heart rate of the patient exceeded the first threshold for at least a first minimum duration 523 determining when the heart rate of the patient exceeded the second threshold for at least a second minimum duration 524 processing the signals to detect atrial fibrillation 525 triggering a first monitoring state if the heart rate of the patient exceeds the first threshold for a first minimum duration, and triggering a second monitoring state if the heart rate of the patient exceeds the second threshold for a second minimum duration, wherein the triggering of the second monitoring state is carried out with ceasing the first monitoring state, wherein timing information pertaining to the at least one first time period is gathered in the first monitoring state, and timing information pertaining to the at least one second time period is gathered in the second monitoring state

*FIG. 4B*

530 providing monitoring results in response to a result of the processing, wherein the monitoring results include information indicative of: (a) the heart rate of the patient during the monitoring period; (b) at least one first time period in which the heart rate of the patient exceeded a first threshold; and (c) at least one second time period in which the heart rate of the patient exceeded both the first threshold and a second threshold 531 providing a first tachycardia indication if the heart rate of the patient was higher than the first threshold for a first tachycardia indicative duration, and providing a second tachycardia indication if the heart rate of the patient was higher than the second threshold that is higher than the first threshold 532 providing a first bradycardia indication if the heart rate of the patient was lower than the first threshold for a first bradycardia indicative duration, and providing a second bradycardia indication if the heart rate of the patient was lower than the second threshold that is lower than the first threshold 533 providing a bradycardia indication, and a pause indication that is indicative of at least one heart beating pause and which is distinct from the bradycardia indication 534 providing a first tachycardia indication if the heart rate of the patient was higher than a first tachycardia threshold for a first tachycardia indicative duration, providing a second tachycardia indication if the heart rate of the patient was higher than a second tachycardia threshold that is higher than the first tachycardia threshold, providing a first bradycardia indication if the heart rate of the patient was lower than a first bradycardia threshold for a first bradycardia indicative duration, and providing a second bradycardia indication if the heart rate of the patient was lower than a second bradycardia threshold that is lower than the first threshold 535 providing the monitoring results that include information pertaining to first time periods that are longer than the first minimum duration 536 providing the monitoring results that include information pertaining to second time periods that are longer than the second minimum duration 537 providing monitoring summary of the monitoring period, that includes a first time summation responsive to times in which the heart rate of the patient exceeded the first threshold for periods longer than a first minimum duration, and a second time summation responsive to times in which the heart rate of the patient exceeded the second threshold for periods longer than a second minimum duration 538 providing information indicative of atrial fibrillation of the heart of the patient during the monitoring period 339 providing results that are responsive to information gathered by at least one additional sensor that is selected from an oxygen saturation sensor, a mechanical sensor, and an environmental sensor

*FIG. 4C*

METHOD AND A SYSTEM FOR CARDIAC MONITORING

RELATED APPLICATIONS

This application is a continuation of U.S. patent application Ser. No. 12/760,569 filing date Apr. 15, 2010 which is incorporated herein by reference.

BACKGROUND OF THE INVENTION

The heart rate is known in the art as an indicator of different kinds of medical conditions. Therefore, different types of heart rate monitors have been provided over the years. However, mere monitoring of the heart rate itself may be of little importance. Furthermore, when the heart rate of the patient shows different behaviors, it may be beneficial to perform additional measurements—which may not be required in normal conditions—in order to acquire more extensive information relating to the health conditions of the patient. Therefore, there is a need for simple and effective systems and methods for cardiac monitoring.

SUMMARY OF THE INVENTION

A method for monitoring a heart of a patient, the method comprising: receiving signals indicative of cardiac activity of the patient during a monitoring period; and processing the signals and providing monitoring results in response to a result of the processing; wherein the monitoring results comprise information indicative of: (a) the heart rate of the patient during the monitoring period; (b) at least one first time period in which the heart rate of the patient exceeds a first threshold; and (c) at least one second time period in which the heart rate of the patient exceeds both the first threshold and a second threshold.

A medical report form, the medical report form comprises: (a) information indicative of a heart rate of a patient during a monitoring period; (b) information indicative of at least one first time period within the monitoring period in which the heart rate of the patient exceeded a first threshold; and (c) information indicative of at least one second time period in which the heart rate of the patient exceeded both the first threshold and a second threshold.

A method for monitoring a patient, the method comprising: receiving signals indicative of a physiological parameter of the patient during a monitoring period; and processing the signals and providing monitoring results in response to a result of the processing; wherein the monitoring results comprise information indicative of: (a) values of the physiological parameter during the monitoring period; (b) at least one first time period in which a value of the physiological parameter exceeded a first threshold; and (c) at least one second time period in which the a value of the physiological parameter exceeded both the first threshold and a second threshold.

A medical report form, the medical report form comprises: (a) information indicative of values of a physical parameter of a patient during a monitoring period; (b) information indicative of at least one first time period in which a value of the physiological parameter exceeded a first threshold; and (c) information indicative of at least one second time period in which the a value of the physiological parameter exceeded both the first threshold and a second threshold.

BRIEF DESCRIPTION OF THE PRESENT INVENTION

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 5:
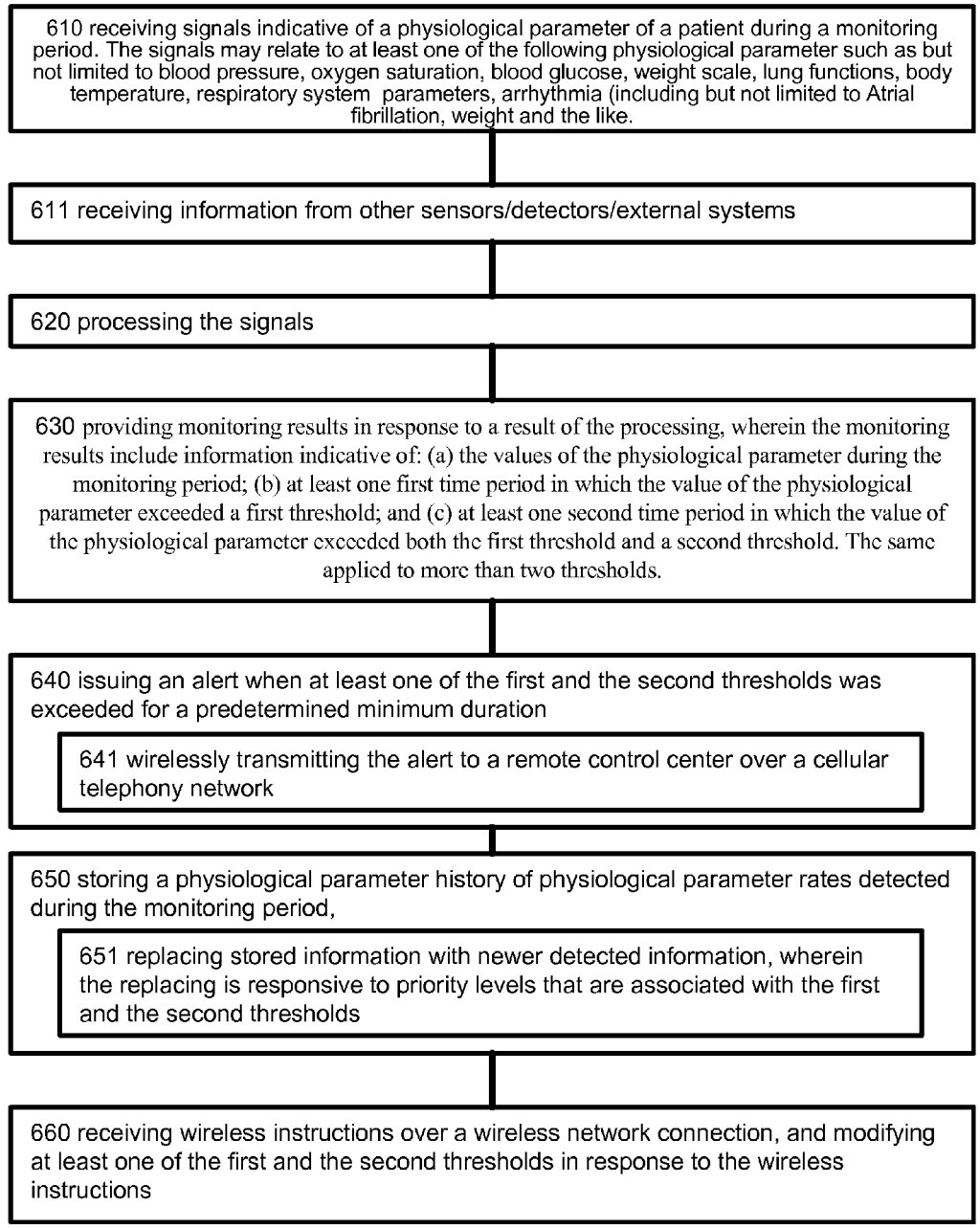

FIGS. 4A, 4B, and 4C illustrate a method for monitoring the heart of a patient, according to an embodiment of the invention; and FIG. 5 illustrates a method for monitoring a physical parameter of a patient, according to an embodiment of the invention.

It will be appreciated that for simplicity and clarity of illustration, elements shown in the figures have not necessarily been drawn to scale or in the specific form factor. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Figure 1A:
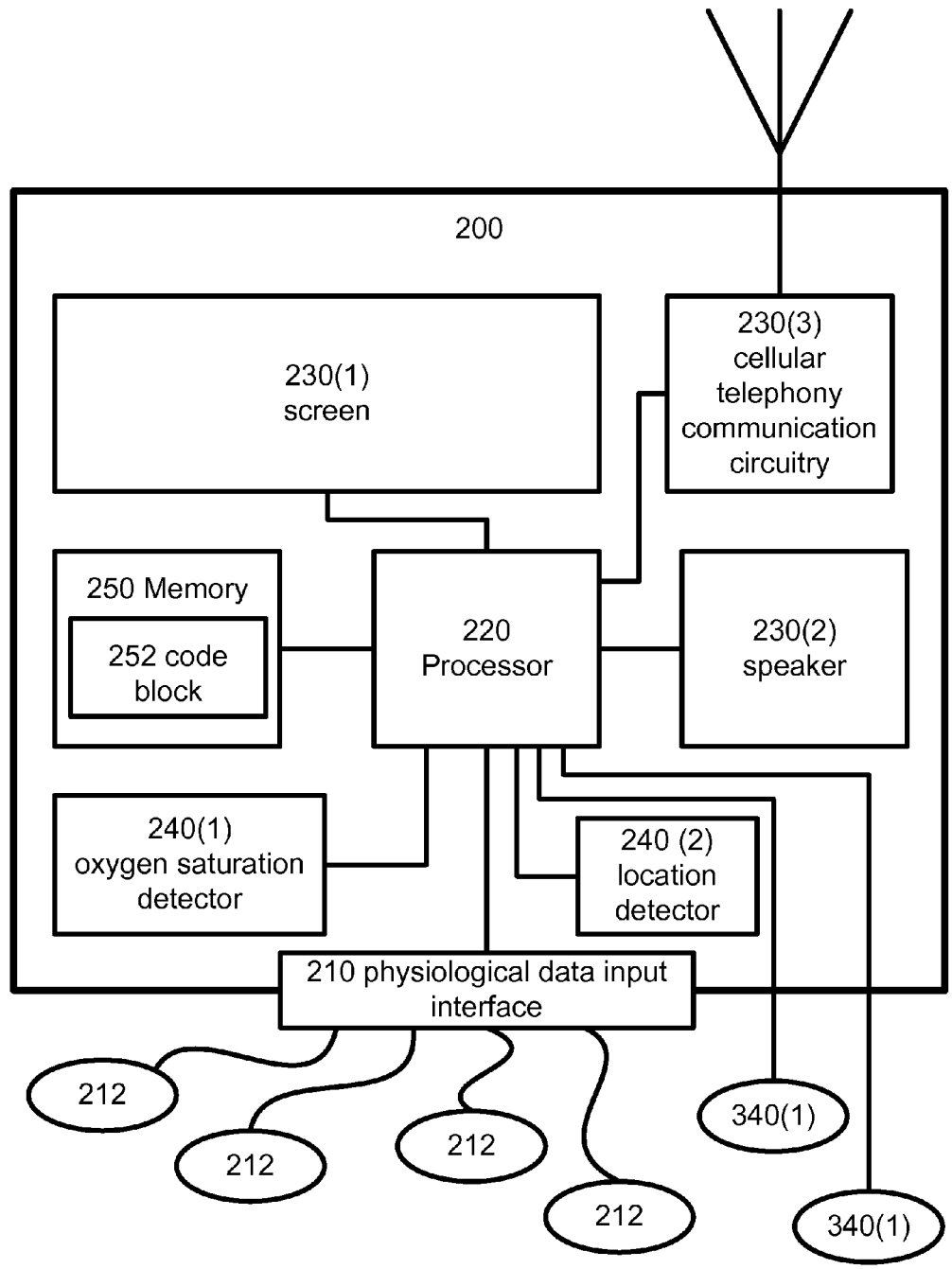
FIG. 1A illustrates a system for monitoring the heart of a patient, according to an embodiment of the invention.

FIG. 1A illustrates system 200 for monitoring the heart of a patient, according to an embodiment of the invention. System 200 includes at least one physiological data input interface 210, operative for receiving signals indicative of cardiac activity of the patient. Physiological data input interface 210 may receive the signals from one or more sensors which may be included in system 200, or may transmit the signals to physiological data input interface 210 (either wireless or over wired connection). For example, the at least one physiological input interface 210 may receive electric signals from multiple electrocardiograph (ECG) electrodes 212 that are placed in different locations on a body of the patient (and which may and may not be a part of system 200). It is however noted that other input devices may be used as well for the detection of signals indicative of the cardiac activity of the patient.

It is further noted that signals received by at least one physiological data input interface 210 may be indicative of different cardiac activity related parameters, many of which are known in the art. For example, some of the parameters which are used in the art (and which may be implemented by system 200) in relation to electrocardiographs are P wave, Q wave, PR/PQ interval, QRS complex, ST segment, T wave, QT interval, and U wave. Other cardiac activity related parameters—which are not necessarily used in relation to ECG, may be implemented as well.

Also, as will be discussed later, according to various embodiments of the invention, system 200 (and more specifically processor 220 discussed below) may utilize other signals that are received from other sensors, detectors, or external system. Such signals may be indicative, for example, of other physiological parameters, of the environment of the patient, and of other parameters (e.g. location, time of the day, etc.).

Such additional signals may be received (and provided to processor 220) via one or more, via an interface shared with physiological data input interface 210, or via independent interface. It is noted that such sensors/detectors may be included in system 200, or may be external to it.

These signals can include signals indicative of at least one of the following physiological parameters of a combination thereof: a blood pressure, oxygen saturation, blood glucose, weight, a lung function parameter, body temperature, a respiratory system parameter, arrhythmia, and Atrial fibrillation, and the like.

Each of these mentioned above physiological parameters can be measured over time (either continuously, in multiple discrete measurements or a combination thereof) and that measured values can be compared to multiple thresholds in order to determine periods during which the measured values exceeded one or more of the thresholds. The amount of thresholds (and their values) may differ from one physiological parameter to the other. The values of the thresholds may differ from one physiological parameter to the other.

System 200 further includes processor 220 configured to process the signals to provide monitoring results, which are discussed below. It is noted that processor 220 may be implemented by hardware, software, firmware, or any combination thereof. It is further noted that processor 220 may be, according to an embodiment of the invention, a multi-purpose processor or a general-use processor. For example, if system 200 is implemented by a hand-held device such as a cellular phone or a personal digital assistant (PDA), a processor of the handheld device may be used as processor 220.

Conveniently, processor 220 may execute instructions stored as computer readable code in within a computer readable medium. Such a computer readable medium may be, for example, memory module 250, or a portion thereof (denoted as code block 252). It is noted that such a computer readable medium may be implemented by hardware.

It is noted that processor 220 may be adapted to execute health monitoring software such as to enable system 200 (alone, or together with a multi-purpose personal data accessory to which it may be connected) to receive the signals, process the signals to provide the monitoring information, and/or to control a long range transmission of the monitoring results to a remote entity.

System 200 further includes at least one output interface 230 that is operative to provide the monitoring results. It is noted that system 200 may include one or more output interfaces 230 of one or more kinds. The monitoring results may be provided by each of the at least one output interfaces 230 in a format comprehendible to human users (e.g. textual output, graphical output, audio output, video output, and any combination thereof), and may also be provided in a machine comprehendible manner (e.g. data formatted according to computer communication protocol, data transmitted over a network connection, and also human comprehendible data which is also machine comprehendible, e.g. textual format). Different examples for output interfaces 230 are illustrated in FIG. 1A—a screen 230(1), a speaker 230(2), and a cellular telephony communication circuitry 230(3). It is however noted that other output interfaces 230 may be used as well.

It is further noted that if multiple output interfaces 230 are implemented in an embodiment of the invention, different portions of the monitoring results (or information responsive to which) may be provided via the different output interface. For example, constant monitoring information may be transmitted to a back-end center using wireless transmissions, while user alerts in danger situations may be provided as sound alarms and/or visual displays.

The monitoring results may include information indicative of: (a) the heart rate of the patient during the monitoring period; (b) at least one first time period in which the heart rate of the patient exceeded a first threshold; and (c) at least one second time period in which the heart rate of the patient exceeded both the first threshold and a second threshold. It is noted that more that two thresholds can be defined and more than two periods can be measured.

It is noted that each of these types of information may be included in the monitoring results in different ways, according to different embodiments of the invention.

For example, the information related to the heart rate of the patient during the monitoring period may include one or more heart rate values measured in one or more points in time within the monitoring period; may include statistical information pertaining to the heart rate (e.g. average, highest and lowest rates), and so forth. It is noted that other types of information pertaining to cardiac activity parameters (such as the parameters discussed in relation to ECG technology) may also be included in the monitoring results.

For example, the information pertaining to the at least one first time period in which the heart rate of the patient exceeded a first threshold may include information to the total time in which the heart rate of the patient exceeded the first threshold, to the duration of each of the one or more first time periods, to the starting and/or ending times of the one or more periods, to the heart rates values during the one or more first time periods, to parameters measured or received by other detector/sensors/external systems (which may and may not be cardiac activity related) during the first time periods, and so forth. Similar information may be included in the monitoring results, by way of example, in relation to the one or more second time periods.

The monitoring results can provide indication relating to other physiological parameters such as but not limited to either one of the following: a blood pressure, oxygen saturation, blood glucose, weight, a lung function parameter, body temperature, a respiratory system parameter, arrhythmia, and Atrial fibrillation, and the like.

It is noted that some or all of the different components of system 200 may be included in a portable housing (which also may provide mechanical support for the different components, as well as possibly protecting the components from various hazards such as mechanical impact, heat, electrical currents, and so forth. Not denoted). The housing may also include interfaces of its own, for connecting it (mechanically or otherwise) to other units. For example, according to an embodiment of the invention, system 200 may be a unit that may be detachably connected to a multi-purpose personal data accessory (such as a cellular phone or a PDA). It is noted that according to such an embodiment of the invention, some of the functionalities of system 200 may be carried out by components of the multi-purpose personal data accessory (e.g. processor, display, power source, communication circuitry, memory, and so forth). It is further noted that according to such an embodiment of the invention, the assembly including the multi-purpose personal data accessory and the add-on unit (if applicable) may be regarded to as a whole as system 200.

Figure 1B:
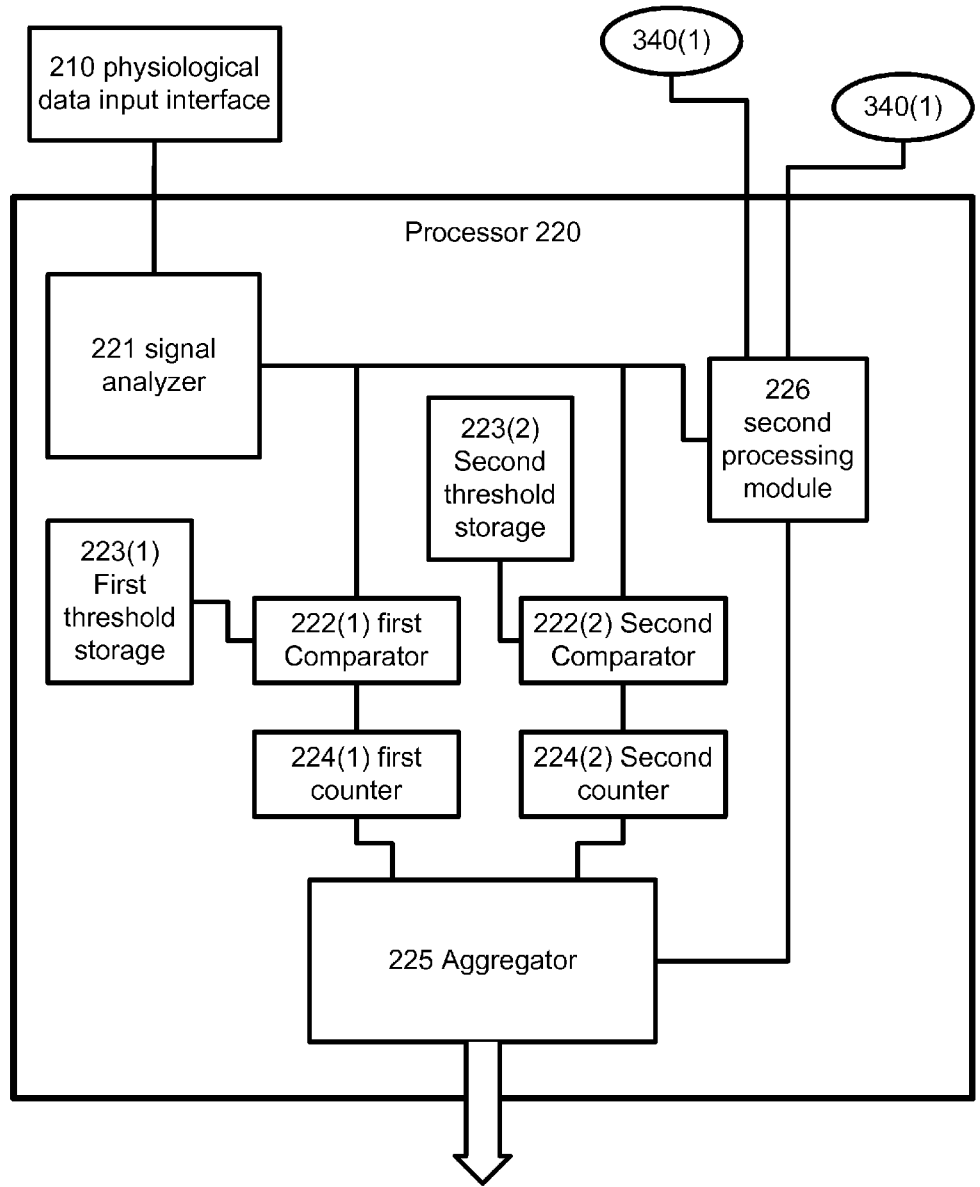
FIG. 1B illustrates a processor of the system for monitoring of the heart rate, according to an embodiment of the invention.

FIG. 1B illustrates processor 220, according to an embodiment of the invention, as well as units which may be connected thereto. Processor 220 may include signal analyzer 221 for preprocessing received signals (e.g. combining signals received from different electrodes 212), e.g. for providing a heart rate signal, if this is not a signal received. The heart rate signal may be provided to one or more comparators 222, which may compare the heart rate signals to the different thresholds (two or more, e.g. at least the first and the second thresholds), for determining whether the heart rate signal has exceeded one or more of the thresholds. The comparing may be against heart rate threshold values which may be stored in one or more threshold storages 223. It is noted that a single comparator 222 may compare the heart rate signal against more than one threshold value.

The results of the one or more comparators 222 may be passed down for one or more counters 224, for counting the number (or duration) of times in which the heart rate exceeded the different thresholds. The results of the comparison/counting may be provided to an aggregator 225 that combines the different results into monitoring results. It is noted that aggregator 225 may also include other information in the monitoring results, e.g. information that is responsive to the results of processing by a second processing module 226, which may process the aforementioned signals as well as signals from other sources (e.g. detectors 340).

Detectors 340 can sense various physiological parameters including but not limited to heart rate, weight, blood pressure, oxygen saturation, blood glucose, lung functions, body temperature, respiratory system parameters, arrhythmia (including but not limited to Atrial fibrillation, and the like).

It is noted that some physiological parameters can be sensed by sensors 340 while information relating to other physiological parameters can be received by physiological data input interface 210.

Whether implemented as in FIG. 1B or otherwise, the processing of the signals, and/or of additional information received by processor 220, may be carried out at different times, according to different embodiments of the invention. Also, different acts of processing (possibly of different processing levels) may be carried out at different times. Such times may be, for example, a continuous real time, or near-real time processing, timed processing at predetermined intervals, processing when processor 220 is relatively free from other processing tasks, processing after the monitoring period is over, and so forth. It is noted that in different situations (which may be related to exceeding of the first and/or the second thresholds), processor 220 may determine to transmit at least a portion of the information gathered to a remote entity (e.g. a control center, over cellular telephony network), for more extensive processing.

According to an embodiment of the invention, the processing of at least a portion of the signal(s) may be carried out by providing the at least portion of the signals multiple times via processor 220 and/or a heart rate analyzer (which may be a portion of processor 220), to determine the total time in which the heart rate exceeded one or more thresholds. Re-running the heart rate may allow for more accurate reporting capabilities, in some embodiments of the invention, of total time recorded spent in the specified rhythm (tachycardia, bradycardia, atrial fibrillation, and the like). Additional more specific measurements may also be determined such as but not limited to high and low heart rate within an episode, length of episode, number of beats within the episode, Heart Rate Variability, etc.

Likewise, the providing of the monitoring information (and/or of different portions of which) may also be carried out at different times, according to different embodiments of the invention. Such times may be but are not limited to, for example, a continuous real time, or near-real time provision, a timed provision at predetermined intervals, a provision when the output interface 230 (or a communication channel associated with which) is relatively free from other tasks, a provision after the monitoring period is over, and so forth.

Some of the conditions which may be detected by system 200, according to corresponding embodiments of the invention, are tachycardia (which may be defined, according to one definition of the term, as a form of cardiac arrhythmia which refers to a rapid beating of the heart) and bradycardia (which may be defined, according to one definition of the term, as an abnormally slow heart beat), atrial fibrillation (which may be defined, according to one definition of the term, as an irregularly irregular heart beat) and Heart Pause (which may be defined, according to one definition of the term, as the temporary cecasion of a heart beat). It is noted that system 200 may be suited for responding to tachycardia situations, to bradycardia situations, to both (as discussed below), to atrial fibrillation and to heart pause situations. System 200 may also detect and respond to other types of cardiac situations, such as heart pausing, and atrial fibrillation (it is noted that, according to an embodiment of the invention, processor 220 is further configured to process the signals to detect atrial fibrillation, and to provide information indicative of atrial fibrillation of the heart of the patient during the monitoring period). These noted conditions may also be detected simultaneously (e.g. atrial fibrillation and tachycardia or bradycardia, atrial fibrillation and pause, bradycardia and pause, tachycardia and pause, etc.).

System 200 can also sense conditions relating to physical parameters such as heart rate, weight, blood pressure, oxygen saturation, blood glucose, lung functions, body temperature, respiratory system parameters, arrhythmia (including but not limited to Atrial fibrillation, and the like). These conditions can be related to values of these physical parameters and to at least one period of time in which these values belonged to a predefined value range (above a thresholds, below a threshold, between thresholds, above multiple thresholds, below multiple thresholds), and the like.

According to an embodiment of the invention, processor 220 is configured to provide a first tachycardia indication if the heart rate of the patient was higher than the first threshold (possibly only if the heart rate was higher than the first threshold for a first tachycardia indicative duration), and to provide a second tachycardia indication if the heart rate of the patient was higher than the second threshold that is higher than the first threshold (possibly only if the heart rate was higher than the second threshold for a second tachycardia indicative duration).

For example, processor 220 may be configured to provide the first tachycardia indication if the heart rate of the patient was higher than the 150 beats per minute (BPM) for more than 10 seconds, and to provide the second tachycardia indication if the heart rate of the patient was higher than 170 BPM for more than 7 seconds. It is noted that the thresholds may be general, may be matched specifically to the patient by processor 220 using different criteria than the standard (e.g. age, cardiac parameters), may be determined by the patient, by a medical practitioner, by an external system, and possibly manipulated by a remote control center (e.g. at the request of a medical practitioner), and so forth. The threshold may also be modified from time to time.

It is noted that processor 220 may also trigger other operations besides the providing of the monitoring results, when providing a tachycardia indication (or other types of indication). For example, when providing the first tachycardia indication, processor 220 may activate additional sensors (e.g.

oxygen level sensors, body temperature sensors, and so forth) and process their inputs and outputs (in order to provide a measurement of biological conditions, physical conditions, environmental conditions, and so forth.), and when providing the second tachycardia indication, processor 220 may trigger an urgency event alert, contacting the control center to call an emergency unit, and so forth. According to an embodiment of the invention any combination of rhythm or rate thresholds and biological or environmental thresholds may activate an alert including contacting the control center to alert emergency services.

The processor can provide monitoring results, trigger another operation besides the provision of a monitoring result, in relation to values of physical parameters such as heart rate, weight, blood pressure, oxygen saturation, blood glucose, lung functions, body temperature, respiratory system parameters, arrhythmia (including but not limited to Atrial fibrillation, and the like). Processor 220 can respond to conditions that can be related to values of these physical parameters and to at least one period of time in which these values belonged to a predefined value range (above a thresholds, below a threshold, between thresholds, above multiple thresholds, below multiple thresholds), and the like.

It is noted that processor 220 may be configured to utilize more than a first and a second tachycardia thresholds—i.e. processor 220 may be configured to utilize three or more tachycardia thresholds. For example, processor 220 may be configured to provide a third (or additional) tachycardia indication if the heart rate of the patient was higher than a third tachycardia threshold (or higher degree threshold) that is higher than both the first and the second thresholds (possibly only if the heart rate was higher than the third threshold for a third tachycardia indicative duration).

Generally, processor 220 may be configured to utilize three or more thresholds including at least the first threshold, the second threshold and at least one additional threshold (wherein whenever the heart rate exceeds the additional threshold, it also exceeds the first and the second threshold), and to provide an exceeding indication if the heart rate of the patient exceeded any of the at least one additional thresholds (possibly only if the heart rate was higher than the additional threshold for a third tachycardia indicative duration). The second, third and other thresholds may also be activated as the first level threshold without necessarily activating the first and second thresholds if the primary indication exceeds the initial one or two thresholds.

According to an embodiment of the invention, processor 220 is configured to provide a first bradycardia indication if the heart rate of the patient was lower than the first threshold (possibly only if the heart rate was lower than the first threshold for a first bradycardia indicative duration), and to provide a second bradycardia indication if the heart rate of the patient was lower than the second threshold that is lower than the first threshold (possibly only if the heart rate was lower than the second bradycardia threshold for a second bradycardia indicative duration).

For example, processor 220 may be configured to provide a first bradycardia indication if the heart rate of the patient was lower than 40 BPM for more than 30 seconds, and to provide a second bradycardia indication if the heart rate of the patient was lower than the 20 BPM for longer than 20 seconds. It is noted that the thresholds may be general, may be matched to the patient by processor 220 using different criteria (e.g. age, cardiac parameters), may be determined by the patient or by a medical practitioner, by a remote control center, and so forth. The threshold may also be modified from time to time.

It is noted that processor 220 may also trigger other operations besides providing of the monitoring results, when providing a bradycardia indication (or other types of indication). For example, when providing the first bradycardia indication, processor 220 may activate additional sensors and process their inputs, and when providing the second bradycardia indication, processor 220 may trigger an urgent event alert, contacting the control center to active the emergency protocol, and so forth. According to an embodiment of the invention any combination of rhythm or rate thresholds and biological or environmental thresholds may activate an alert including contacting the control center to activate emergency protocol.

It is noted that processor 220 may be configured to utilize more than a first and a second bradycardia thresholds, i.e. processor 220 may be configured, according to an embodiment of the invention, to utilize three or more bradycardia thresholds. For example, processor 220 may be configured to provide a third (or additional) bradycardia indication if the heart rate of the patient was lower than a third bradycardia threshold (or lower degree threshold) that is lower than both the first and the second thresholds (possibly only if the heart rate was lower than the third threshold for a third bradycardia indicative duration). The second, third and other thresholds may also be activated as the first level threshold without necessarily activating the first and second thresholds if the primary indication exceeds the initial one or two thresholds.

It is noted that, according to an embodiment of the invention, processor 220 may detect heart pauses distinctively from the detection of bradycardia. According to an embodiment of the invention, processor 220 is further configured to process the signals to detect heart pauses, wherein the output interface is further operative to provide a bradycardia indication, and a pause indication, wherein the pause indication is indicative of at least one heart pause and which is distinct from the bradycardia indication. According to an embodiment of the invention, the providing of those various indications is a result of multiple simultaneous (or partly simultaneous) signal processing processes.

It is further noted that according to an embodiment of the invention, system 200 may be configured to detect both tachycardia and bradycardia, wherein in such an embodiment of the invention, a first and a second thresholds are defined for each of the conditions—a first and a second tachycardia threshold which may be a higher than expected heart rate, and a first and a second bradycardia thresholds which may be a lower than expected heart rate.

According to an embodiment of the invention, processor 220 is configured to provide a first tachycardia indication if the heart rate of the patient was higher than a first tachycardia threshold for a first tachycardia indicative duration, to provide a second tachycardia (and third, etc.) indication if the heart rate of the patient was higher than a second tachycardia threshold that is higher than the first tachycardia threshold, to provide a first bradycardia indication if the heart rate of the patient was lower than a first bradycardia threshold for a first bradycardia indicative duration, and to provide a second bradycardia (and third, etc.) indication if the heart rate of the patient was lower than a second bradycardia threshold that is lower than the first threshold.

According to an embodiment of the invention in which processor 220 is configured to determine when the heart rate of the patient exceeded the first threshold for at least a first minimum duration (e.g. as exemplified above), processor 220 (and/or output interface 230) may be configured to provide the monitoring results that include information pertaining to first time periods that are longer than the first minimum duration. It is however noted that according to other embodiments of the invention, the time periods which are reported are not bound by any minimum duration other than those indicated by the set parameters on processor 220, and may be configured separately if different than the standard. They may also be manipulated remotely from the control center as requested by the medical practitioner.

According to an embodiment of the invention, processor 220 is further configured to determine when the heart rate of the patient exceeded the second threshold for at least a second minimum duration, and to provide the monitoring results that include information pertaining to second time periods that are longer than the second minimum duration (and third, etc.). It is however noted that according to other embodiments of the invention, the time periods which are reported are not bound by any minimum duration other than those indicated by the set parameters on processor 220, and may be configured separately if different than the standard. They may also be manipulated remotely from the control center as requested by the medical practitioner.

For example, if the heart rate of the patient exceeded one of the thresholds for a relatively short period of time (e.g. two or three seconds), this exceeding may not be accounted for in the monitoring results.

According to an embodiment of the invention, processor 220 may be configured to process the signals and/or additional information to detect some or all of the following situations: Supraventricular Tachycardia, Ventricular Tachycardia, shape and/or morphology change, Atrial Flutter, ST segment analysis and alarm, QT analysis and alarm, premature ventricular contractions, premature atrial contractions, heart rate variability, T-waves alternans, and the like. It is noted that in various embodiments of the invention, processor 220 may be configured to process the signals and/or additional information to detect other types of situations as well. It may also be configured for a specific combination of signal detection with two or more of the signal processors.

It is noted that the different indications issued by processor 220 in response to exceeding of one of the threshold may result in different actions, both by system 200 (or some component thereof), by external systems and/or components that are notified about the indications, or by the user or other people such as medical staff. For example, some of the actions which may be taken by system 200 are storing of such information, switching to a different monitoring mode, alerting the user or a remote entity, collecting corresponding data from different sensors, retrieving additional data from the same sensor, and so forth. Other examples for actions which may result from such indications are the call of an ambulance, activation of the emergency protocol, or the alert of the control center, sound an alarm, and so forth.

According to an embodiment of the invention, the output interface (e.g. 230(1), 230(2), 230(3), or other output interface of system 200) is further operative to issue an alert (autonomously, or in response to a command issued by processor 220) when at least one of the first and the second thresholds (or additional thresholds) was exceeded for a predetermined minimum duration. It is noted that the predetermined minimum duration may not be identical to the corresponding minimum duration discussed above. For example, processor 220 may provide indication that the first threshold was exceeded after 20 seconds of exceeding (e.g. in order to trigger an internal storing of cardiac activity relation information), but an alert to an external entity may be issued only if the heart rate of the patient exceeds the threshold for a different set duration (e.g. one minute).

The alert may be issued, according to an embodiment of the invention, to the patient (or to a user of system 200, if different than the patient—(e.g. if operated by a medical staff in a skilled nursing facility), or to a single/multiple remote entities (e.g. control center), and so forth.

According to an embodiment of the invention, system 200 is further operative to wirelessly transmit the alert to a remote control center over a cellular telephony network (e.g. by cellular telephony communication circuitry 230(3)). It is noted that according to various embodiments of the invention, system 200 may be further operative to transmit the alert to a remote entity over one or more connections (e.g. network connection, point-to-point connection, and so forth)—wherein any one of those one or more connections may be either wireless or (in some situations, e.g. during monitoring in a field clinic) wired connection. Such communication (both outgoing and incoming) may be enabled, according to various embodiments of the invention, by one or more communication circuitries and may also allow the manipulation or activation of such thresholds.

It is noted that system 200 may be used for providing monitoring summary of entire monitoring period (e.g. a daily summary, a weekly summary, trending reports and so forth). It is noted that the providing of such summary need not necessarily mean that the monitoring is ceased. This summary data may be programmed at set intervals into the system such as, but not limited to processor 220 or manually retrieved by request. It is noted that the monitoring summary may include different sorts of cardiac activity related information (e.g. as discussed in relation to the monitoring results), as well as other types of information (e.g. information gathered from other sensors, detectors, and/or external systems—such as but not limited to the components discussed above and may be any combination or variation thereof) and may be accessed remotely or via a wired connection.

According to an embodiment of the invention, processor 220 is further configured to provide a monitoring summary of the monitoring period, that includes a first time summation responsive to an aggregate duration of at least one period during which the heart rate of the patient exceeded the first threshold for periods longer than a first minimum duration, and a second time summation responsive to times in which the heart rate of the patient exceeded the second threshold for periods longer than a second minimum duration (and possibly to an aggregate duration of at least one such period). For example, the monitoring summary may indicate that in the past week, the heart rate of the patient exceeded 150 BPM for 7:32 hours (counting only consecutive periods longer than 10 seconds), and exceeded 170 BPM for 0:32 hours (counting only consecutive periods longer than 7 seconds or duration as set or requested by the medical practitioner).

It is noted that the first time summation may or may not relate to periods accounted for in the second time summation. According to an embodiment of the invention, processor 220 is configured to trigger a first monitoring state if the heart rate of the patient exceeds the first threshold for a first minimum duration, and to trigger a second monitoring state if the heart rate of the patient exceeds the second threshold for a second minimum duration, wherein the triggering of the second monitoring state involves ceasing the first monitoring state, wherein timing information pertaining to the at least one first time period is gathered in the first monitoring state, and timing information pertaining to the at least one second time period is gathered in the second monitoring state.

According to an embodiment of the invention, system 200 includes memory module 250, which may be operative to store a history of heart rate values detected during the monitoring period. Since the storage capacity of memory module 250 may be limited, according to an embodiment of the invention, memory module 250 may replace stored information with newer detected information. E.g. memory module 250 may be configured to store heart rate information of the last few hours—e.g. six hours (previous information may be discarded, and/or transmitted to an external storage). According to an embodiment of the invention, memory module 250 is configured to replace stored information in response to priority levels that are associated with the first and the second thresholds. For example, heart rate recordings of periods in which the heart rate exceeded the first and/or the second threshold may be stored for longer period comparing to "regular" heart rates.

According to an embodiment of the invention, system 200 includes a wireless communication module that is connected to processor 220 (which may be cellular telephony communication circuitry 230(3), or other communication module which may utilize another type of wireless communication). The wireless communication module may be operative to receive wireless instructions over a wireless network connection, wherein processor 220 is further configured to modify at least one of the first and the second thresholds in response to the wireless instructions. For example, such instructions may be received by a short messaging service (SMS) message, or by software downloading. It is noted that according to various embodiments of the invention, such instructions may also be received otherwise, e.g. using wired connection (e.g. a USB interface), or an interface of system 200 (e.g. using a keypad or other control accessible to the patient or medical practitioner).

According to an embodiment of the invention, system 200 may include a wireless communication module (or a wired communication module) for transmitting data (e.g. physiological data, monitoring results) for storage and/or analysis by an external system (e.g. a server, a medical center unit, and so forth). According to various embodiments of the invention, such information may be transmitted to that external system during monitoring or after the monitoring ceased. It is noted that the external system may be a dedicated system (include dedicated hardware, software, and/or firmware) for processing such information, and may be a part of a combined system that include that external system and one or more systems 200.

According to an embodiment of the invention, processor 220 is further configured to provide monitoring results that are responsive to information gathered by at least one additional sensor that is selected from an oxygen saturation sensor, a mechanical sensor, and an environmental sensor.

According to various embodiments of the invention, system 200 (and especially processor 220) may utilize other signals apart from those which are indicative of the cardiac activity, which may be received from other sensors, detectors, or external system. Such signals may be indicative, for example, of other physiological parameters, of an environment of the patient, and/or of other parameters (e.g. location, time of the day, etc.). Such additional signals may be received (and provided to processor 220) via at least one or more, via an interface shared with physiological data input interface 210, or via independent interface. It is noted that such sensors/detectors may be included in system 200, or may be external to it.

It is noted that processor 220 may process the additional information together with the cardiac activity information and/or independent of which. It is noted that processor 220 may process the signals indicative of the cardiac activity in response to (or in light of) information received from other source. Furthermore, processor 220 may modify a monitoring state in different conditions (e.g. when exceeded a lower/higher threshold, or if exceeding for less or more minimal duration), may provide exceeding indication, or otherwise provide different monitoring results and/or summary, in response to the additional information.

For example, if the heart rate of the patient rose abruptly, a mechanical sensor (e.g. an accelerometer) and/or a location sensor may be used to determine that the patient is likely involved in a physical activity, and thus the rising in heart rate is not due to a tachycardia incident. Also, in another example, a detection of pollution in the air surrounding the patient may also be detected when the heart rate exceeds a threshold, in which case an alternative alert may be issued, advising the patient to move to a less polluted area.

Some of the additional sensors/detectors which may be used in different embodiments of the invention are sensor including but not limited to detecting O2 saturation, blood glucose level, blood pressure, weight, etc. and/or mechanical sensors relating to movements of the patient, temperatures of the patient (bodily) and/or of the environment, location of the patient (e.g. GPS), concentration of different materials (e.g. pollutants) in the environment of the patient, and so forth.

It is noted that processor 220 may also process the cardiac activity and possibly also such additional information in further view of historical data gathered—e.g. in view of past heart rate of the patient, of past oxygen saturation levels, and so forth. As such, not only may acute alerts for an existing condition cause an alert but also trended data (signals as processed by system 200 and processor 220, etc.) based on changes and compared through historical data may cause such an alert to such entities but not limited to the patient, the medical practitioner, the control center, etc.

It is noted that system 200 may include one or more such additional sensors/detectors 240, e.g. oxygen saturation detector 240(1), location detector 240(2), and so forth. As aforementioned, processor 220 may also receive such information from external sensors/detector/systems 340, such as mechanical sensors 340(1).

According to an embodiment of the invention, system 200 may include a controllable sensor and/or a configurable sensor (e.g. a sensor 240) or be connected to such a controllable and/or configurable sensor (e.g. a sensor 340), wherein processor 220 is configured to process at least the signals indicative of the cardiac activity (and possibly signals from other sensors but the controllable sensor), and to activate the controllable and/or configurable sensor in response to a result of the processing.

According to an embodiment of the invention, system 200 includes a sensor 240 or is connected to an external sensor 340, wherein processor 220 may be configured to process signals as aforementioned, and to control a long range transmission of the monitoring results to a remote entity, so as to selectively control a long rage transmission of processed data of the sensor in response to a result of the processing (e.g. in order to reduce band width constrains). For example, processor 220 may choose to transmit a narrow-band transmission when the results of the processing are within predefined norm limits, and to transmit more bandwidth-consuming information from the sensor if the results of the processing exceed those limits.

According to an embodiment of the invention, system 200 may be capable of detecting increase of heart rate for defined monitoring period.

According to an embodiment of the invention, system 200 may be capable of detecting decrease of heart rate for defined monitoring period.

According to an embodiment of the invention, system 200 may be capable of measuring duration of heart pauses.

According to an embodiment of the invention, system 200 may be capable of detection of Atrial fibrillation (AFIB).

According to an embodiment of the invention, system 200 may be capable of detecting tachycardia for first defined period and reporting on it. According to an embodiment of the invention, system 200 may be further capable of detecting tachycardia for second defined period and reporting on it. According to an embodiment of the invention, system 200 may be further capable of detecting tachycardia for third and so on defined period and reporting on it According to an embodiment of the invention, system 200 may be capable of detecting bradycardia for first defined period and reporting on it. According to an embodiment of the invention, system 200 may be further capable of detecting bradycardia for second defined period and reporting on it. According to an embodiment of the invention, system 200 may be further capable of detecting bradycardia for third and so on defined period and reporting on it According to an embodiment of the invention, system 200 may be capable of detecting pause for first defined duration and reporting on it. According to an embodiment of the invention, system 200 may be further capable of detecting pause for second and so on defined duration and reporting on it.

According to an embodiment of the invention, system 200 may be capable of detecting tachycardia for first defined period and AFIB for independently defined time period and reporting both tachycardia and AFIB According to an embodiment of the invention, system 200 may be capable of detecting tachycardia for second defined period and AFIB for independently defined time period and reporting both tachycardia and AFIB According to an embodiment of the invention, system 200 may be capable of detecting tachycardia for third and so on defined period and AFIB for independently defined time period and reporting both tachycardia and AFIB According to an embodiment of the invention, system 200 may be capable of detecting bradycardia for first defined period and AFIB for independently defined time period and reporting both bradycardia and AFIB According to an embodiment of the invention, system 200 may be capable of detecting bradycardia for second defined period and AFIB for independently defined time period and reporting both bradycardia and AFIB According to an embodiment of the invention, system 200 may be capable of detecting bradycardia for third and so on defined period and AFIB for independently defined time period and reporting both bradycardia and AFIB According to an embodiment of the invention, system 200 may be capable of detecting tachycardia for first defined period of time and pause for independently defined period of time According to an embodiment of the invention, system 200 may be capable of detecting tachycardia for second defined period of time and pause for independently defined period of time According to an embodiment of the invention, system 200 may be capable of detecting tachycardia for third and so on defined period of time and pause for independently defined period of time According to an embodiment of the invention, system 200 may be capable of detecting any of the multiple thresholds for tachycardia, with AFIB and any threshold for heart pause for defined time period simultaneously.

According to an embodiment of the invention, system 200 may be capable of detecting any multiple thresholds for bradycardia, with AFIB and any threshold for heart pause for defined time period simultaneously.

Figure 2A:
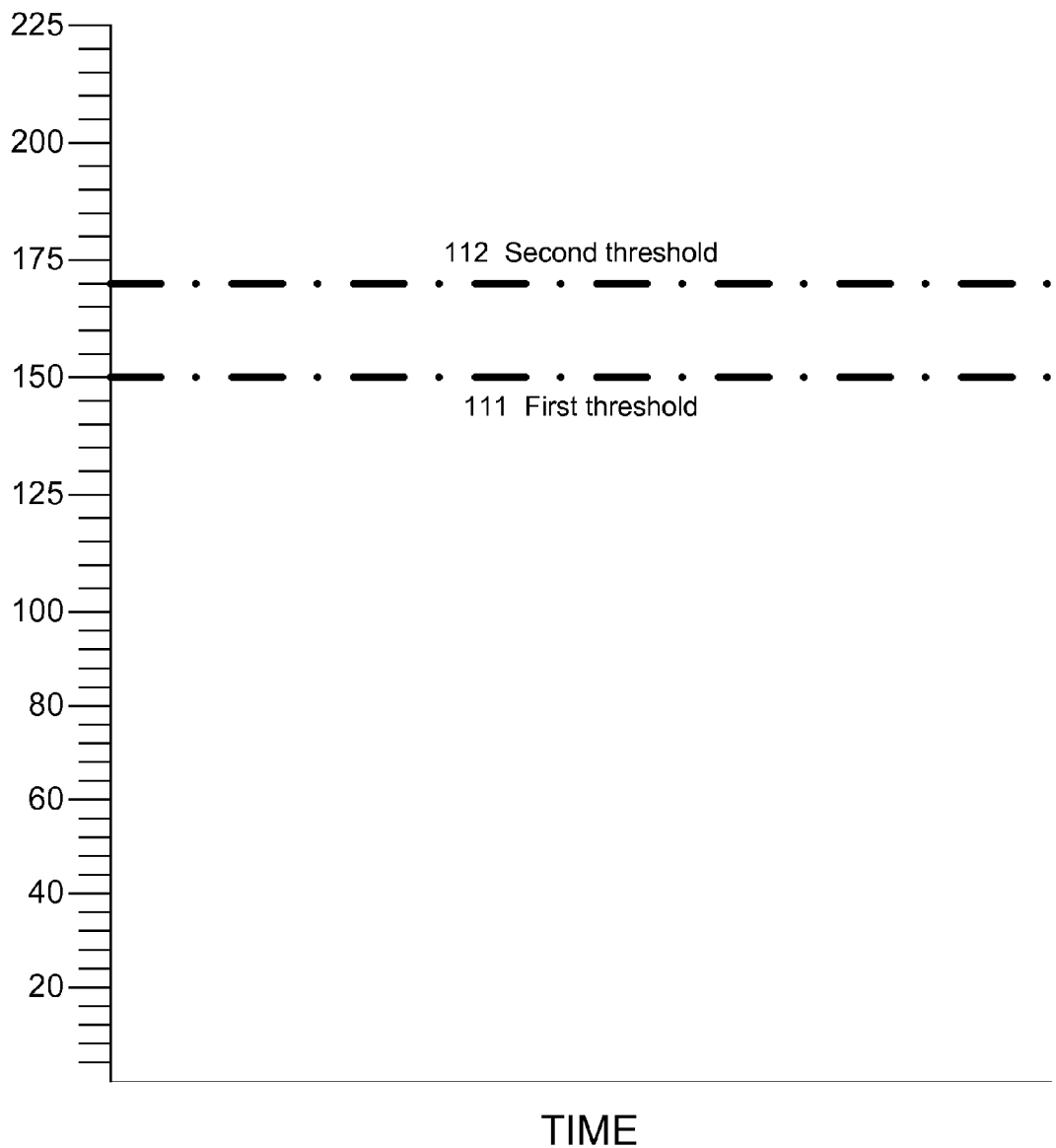
FIGS. 2A, 2B and 2C illustrate heart rate monitoring schemes, according to various embodiment of the invention.
Figure 2B:
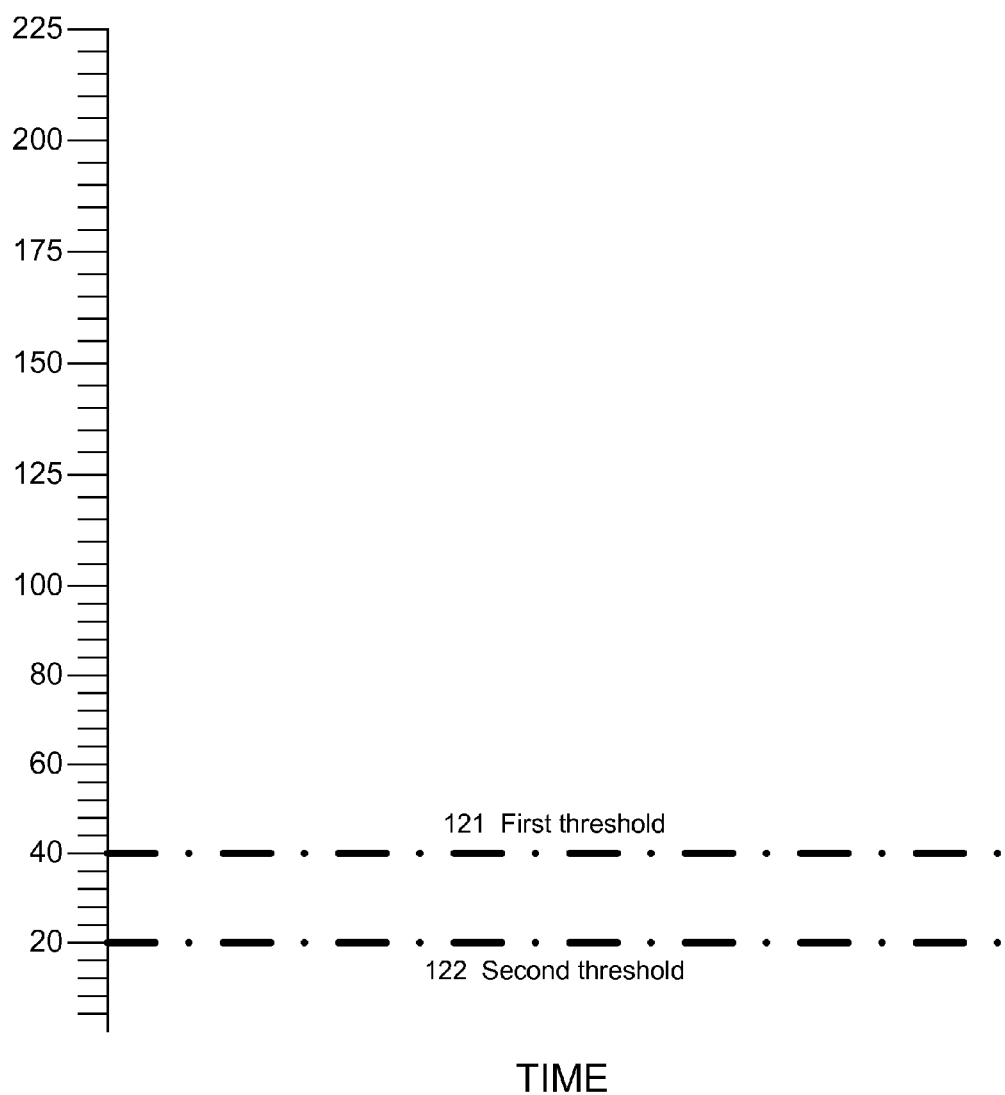
Figure 2C:
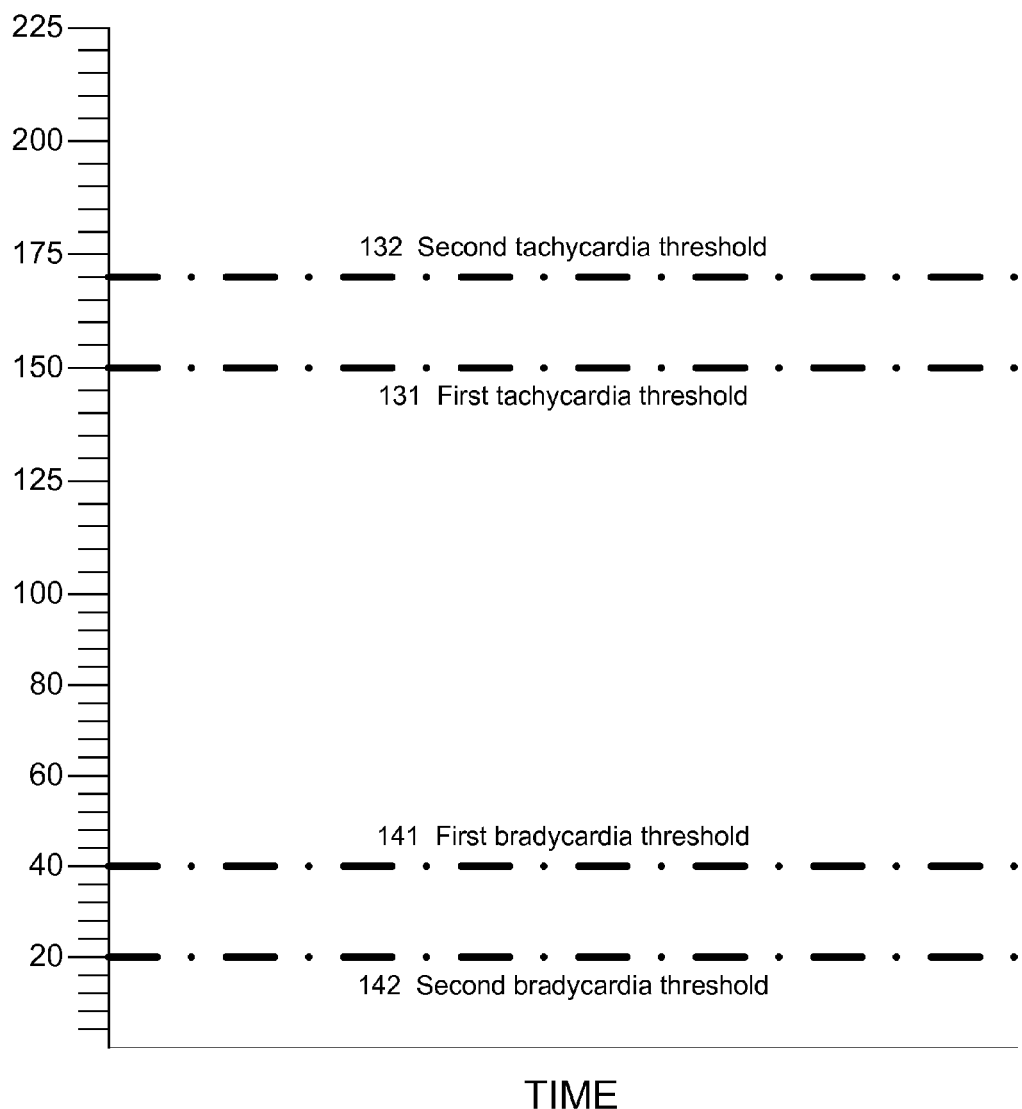

FIGS. 2A, 2B and 2C illustrate heart rate monitoring scheme, according to various embodiment of the invention. FIG. 2A illustrates heart rate monitoring scheme 101 in which the first threshold 111 is 150 beats per minute, and the second threshold 112 is 170 beats per minute. Any heart rate that is higher than the first and/or the second thresholds 111 and 112 exceeds the corresponding threshold. It is noted that a minimum exceeding duration may be associated with each of the thresholds, e.g. as discussed above. According to an embodiment of the invention, system 200 may implement heart rate monitoring scheme 101.

FIG. 2B illustrates heart rate monitoring scheme 102 in which the first threshold 121 is 40 beats per minute, and the second threshold 122 is 20 beats per minute. Any heart rate that is lower than the first and/or the second thresholds 121 and 122 exceeds the corresponding threshold. It is noted that a minimum exceeding duration may be associated with each of the thresholds, e.g. as discussed above. According to an embodiment of the invention, system 200 may implement heart rate monitoring scheme 102.

FIG. 2C illustrates heart rate monitoring scheme 103 in which two sets of thresholds are present—the first tachycardia threshold 131 is 150 beats per minute, the second tachycardia threshold 132 is 170 beats per minute, the first bradycardia threshold 141 is 40 beats per minute, and the second bradycardia threshold 142 is 20 beats per minute. Any heart rate that is higher than the first and/or the second tachycardia thresholds 131 and 132 exceeds the corresponding tachycardia threshold, while any heart rate that is lower than the first and/or the second thresholds 141 and 142 exceeds the corresponding bradycardia threshold. It is noted that a minimum exceeding duration may be associated with each of the thresholds, e.g. as discussed above. According to an embodiment of the invention, system 200 may implement heart rate monitoring scheme 103.

Regarding all the minimum durations, it is noted that other minimum durations may be defined—wherein if during an episode in which a threshold is exceeded (e.g. the first threshold), a heart rate that does not exceed the threshold is measured for under another minimum duration (which may be relatively short, e.g. one or two seconds), the exceeding of the threshold is regarded as continuous.

Figure 3:
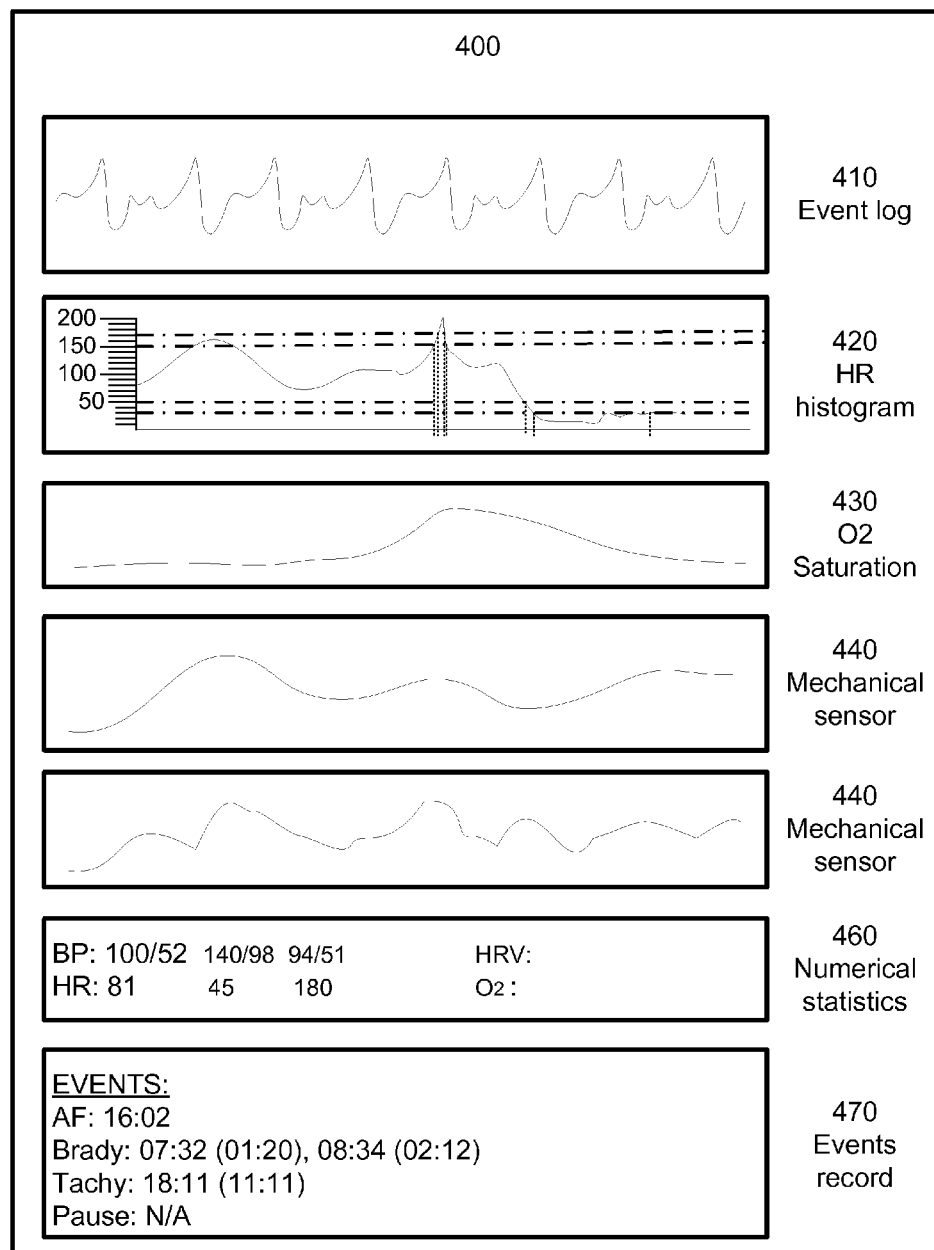
FIG. 3 illustrates medical report form according to an embodiment of the invention.

FIG. 3 illustrates monitoring results, according to an embodiment of the invention. The monitoring results presented in FIG. 3 are presented in a graphical manner, but it is noted that non-graphical monitoring results may also be used.

It is noted that the monitoring results may be included in medical report form 400, according to an embodiment of the invention. Medical report form 400 (or the otherwise provided monitoring results) may include some or all of the following monitoring results portions, as well as possibly other types of information:

i. Event log 410, providing a graphical and/or numerical representation of cardiac activity;
ii. Heart rate histogram 420, providing a graphical and/or numerical representation of heart rate values at different times during the monitoring period;
iii. Saturation strip 430, providing a graphical and/or numerical representation of saturation of one or more materials (e.g. saturation of oxygen $O_2$) in the blood of the patient (usually detected by a matching sensor);
iv. Mechanical sensor information 440, providing a graphical and/or numerical representation of information detected by a mechanical sensor. Information from different sensors (e.g. environmental and/or location sensors) may be presented in a similar manner.

v. Heart rate variability strip 450, providing a graphical and/or numerical representation of heart rate variability, e.g. calculated by a processor such as processor 220;

vi. Numerical statistics portion 460, in which numerical information and/or analysis of different monitored values (e.g. as discussed above) is presented;

vii. Events record 470, providing a graphical and/or numerical representation of times and duration of cardiac events.

According to an embodiment of the invention, medical report form 400 may include at least: (a) information indicative of the heart rate of a patient during a monitoring period; (b) information indicative of at least one first time period within the monitoring period in which the heart rate of the patient exceeded the first threshold; and (c) information indicative of at least one second time period in which the heart rate of the patient exceeded both the first threshold and a second threshold.

According to an embodiment of the invention, medical report form 400 may further include information indicative of cardiac events, which is responsive to the exceeding of at least one of the first and the second thresholds. It is noted that medical report form 400 may include any other type of information which is mentioned as gathered, received, acquired, processed, or provided, in a graphical manner, textual manner, auditory manner, and so forth in any combination of the collected data.

According to various embodiments of the invention medical report 400 can include (a) information indicative of values of a physical parameter of a patient during a monitoring period; (b) information indicative of at least one first time period in which a value of the physiological parameter exceeded a first threshold; and (c) information indicative of at least one second time period in which the a value of the physiological parameter exceeded both the first threshold and a second threshold. The medical report can include information pertaining to additional time periods in which additional thresholds were exceeded.

The physiological parameter can be at least one of the following: a blood pressure, oxygen saturation, blood glucose, weight, a lung function parameter, body temperature, a respiratory system parameter, arrhythmia, and Atrial fibrillation.

It is noted that, according to various embodiments of the invention, the monitoring results may be provided with (or via) an interface that enables a recipient of the monitoring results to select which results and/or portions of results to provide (e.g. selecting information from which sensors will be displayed, focusing of specific time period, and so forth as well as request additional data). According to an embodiment of the invention, some of the processing may result from a recipient selection, so that processor 220 may, for example, process additional information to provide required monitoring results.

FIGS. 4A, 4B, and 4C illustrate a method 500 for monitoring a heart of a patient, according to an embodiment of the invention. It is noted that, method 500 may be implemented by system 200 and/or by different components thereof, and that embodiments of system 200 may be implemented using corresponding stages of method 500, even if not explicitly so elaborated.

Method 500 may start with stage 510 of receiving signals indicative of cardiac activity of the patient during a monitoring period. The signals may be ECG signals, but this is not necessarily so. Referring to the examples set forth in the previous drawings, the receiving may be carried out by a physiological data input interface such as physiological data input interface 210.

It is noted that method 500 may also include stage 511 of receiving of information from other sensors, detectors, and/or external system, e.g. relating to other bodily activities and/or status, to environment of the patient, to location of the patient, to mechanical movements of the patient, and so forth.

Method 500 further includes stage 520 of processing the signal, which may also include processing of additional information. The processing of stage 520 may conveniently include processing the signals and possibly additional information received in stage 511 to provide the monitoring results of stage 530. Referring to the examples set forth in the previous drawings, the processing may be carried out by a processor such as processor 220.

It is noted that the processing may be carried out during the monitoring period, and/or after it is over, according to various embodiments of the invention, e.g. as discussed above in relation to the processing by processor 220.

The processing may include stage 521 of processing the signals to detect heart pauses.

The processing may include stage 522 of determining when the heart rate of the patient exceeded the first threshold for at least a first minimum duration (wherein the exceeding heart rate may be either higher or lower than the first threshold, where applicable, as discussed above).

The processing may include stage 523 of determining when the heart rate of the patient exceeded the second threshold for at least a second minimum duration.

The processing may include stage 524 of processing the signals to detect atrial fibrillation.

The processing may include stage 525 of triggering a first monitoring state if the heart rate of the patient exceeds the first threshold for a first minimum duration, and triggering a second monitoring state if the heart rate of the patient exceeds the second threshold for a second minimum duration, wherein the triggering of the second monitoring state involves ceasing the first monitoring state, wherein timing information pertaining to the at least one first time period is gathered in the first monitoring state, and timing information pertaining to the at least one second time period is gathered in the second monitoring state.

Method 500 further includes stage 530 of providing monitoring results in response to a result of the processing, wherein the monitoring results include information indicative of: (a) the heart rate of the patient during the monitoring period; (b) at least one first time period in which the heart rate of the patient exceeded a first threshold; and (c) at least one second time period in which the heart rate of the patient exceeded both the first threshold and a second threshold.

Referring to the examples set forth in the previous drawings, the providing of the monitoring results may be carried out by an output interface such as output interfaces 230, 230(1), 230(2), and/or 230(3).

It is noted that the providing may be carried out during the monitoring period, and/or after it is over, according to various embodiments of the invention, e.g. as discussed above in relation to the providing by output interface 230.

The providing may include stage 531 of providing a first tachycardia indication if the heart rate of the patient was higher than the first threshold for a first tachycardia indicative duration, and providing a second tachycardia indication if the heart rate of the patient was higher than the second threshold that is higher than the first threshold.

The providing may include stage 532 of providing a first bradycardia indication if the heart rate of the patient was lower than the first threshold for a first bradycardia indicative duration, and providing a second bradycardia indication if the heart rate of the patient was lower than the second threshold that is lower than the first threshold.

The providing may include stage 533 of providing a bradycardia indication, and a pause indication, wherein the pause indication is indicative of at least one heart pause and is distinct from the bradycardia indication. According to an embodiment of the invention, the providing of those various indication is a result of multiple simultaneous (or partly simultaneous) signal processing processes.

The providing may include stage 534 of providing a first tachycardia indication if the heart rate of the patient was higher than a first tachycardia threshold for a first tachycardia indicative duration, providing a second tachycardia indication if the heart rate of the patient was higher than a second tachycardia threshold that is higher than the first tachycardia threshold, providing a first bradycardia indication if the heart rate of the patient was lower than a first bradycardia threshold for a first bradycardia indicative duration, and providing a second bradycardia indication if the heart rate of the patient was lower than a second bradycardia threshold that is lower than the first threshold.

The providing may include stage 535 of providing the monitoring results that include information pertaining to first time periods that are longer than the first minimum duration.

The providing may include stage 536 of providing the monitoring results that include information pertaining to second time periods that are longer than the second minimum duration.

The providing may include stage 537 of providing monitoring summary of the monitoring period, that includes a first time summation responsive to times in which the heart rate of the patient exceeded the first threshold for periods longer than a first minimum duration, and a second time summation responsive to times in which the heart rate of the patient exceeded the second threshold for periods longer than a second minimum duration.

The providing may include stage 538 of providing information indicative of atrial fibrillation of the heart of the patient during the monitoring period.

The providing may include stage 339 of providing results that are responsive to information gathered by at least one additional sensor that is selected from a list which includes: an oxygen saturation sensor, a mechanical sensor, and an environmental sensor. According to an embodiment of the invention, the list may include additional sensors, but this is not necessarily so.

Method 500 may further include stage 540 of issuing an alert when at least one of the first and the second thresholds was exceeded for a predetermined minimum duration.

The issuing may include stage 541 of wirelessly transmitting the alert to a remote control center over a cellular telephony network Method 500 may further include stage 550 of storing a heart rate history of heart rates detected during the monitoring period, wherein the storing may include stage 551 of replacing stored information with newer detected information, wherein the replacing of stage 551 is responsive to priority levels that are associated with the first and the second thresholds.

Method 500 may further include stage 560 of receiving wireless instructions over a wireless network connection, and modifying at least one of the first and the second thresholds in response to the wireless instructions.

According to an embodiment of the invention, the providing of the monitoring results may further include providing the monitoring results that further includes information indicative of at least one exceeding time period in which the heart rate of the patient exceeded the first threshold, the second threshold, and at least one additional threshold.

According to an embodiment of the invention, the issuing may further include issuing an alert when at least one of the at least one additional thresholds was exceeded for a predetermined minimum duration.

It is noted that the invention may implement three, four, five, six, or more thresholds. According to some embodiments of the invention, some of the thresholds may not be predetermined, and may be determined (or updated) in response to dynamically determined results. For example—if the first threshold was exceeded for a prolonged period, the second threshold may be updated to a lower or higher value than was set before.

Some of the mentioned above descriptions were made in the context of measurement of heart rate and a comparison of the heart rate to multiple thresholds. It is noted that the mentioned above methods and systems can be applied mutatis mutandis to other physical parameters such as but not limited to blood pressure, oxygen saturation, blood glucose, weight scale, lung functions, body temperature, respiratory system parameters, arrhythmia (including but not limited to Atrial fibrillation, weight and the like.

System 200 can include one or multiple sensors for sensing one or more of these physical parameters.

FIG. 5 illustrate method 600 for monitoring a physical parameter of a patient, according to an embodiment of the invention.

Method 600 may start with stage 610 of receiving signals indicative of a physiological parameter of the patient during a monitoring period. The signals may relate to at least one of the following physiological parameter such as but not limited to blood pressure, oxygen saturation, blood glucose, lung functions, body temperature, respiratory system parameters, arrhythmia (including but not limited to Atrial fibrillation, weight and the like.

It is noted that method 600 may also include stage 611 of receiving of information from other sensors, detectors, and/or external system, e.g. relating to other bodily activities and/or status, to environment of the patient, to location of the patient, to mechanical movements of the patient, and so forth.

Method 600 further includes stage 620 of processing the signal (or signals), which may also include processing of additional information. The processing of stage 620 may conveniently include processing the signals and possibly additional information received in stage 611 to provide the monitoring results of stage 630. Referring to the examples set forth in the previous drawings, the processing may be carried out by a processor such as processor 220.

It is noted that the processing may be carried out during the monitoring period, and/or after it is over, according to various embodiments of the invention, e.g. as discussed above in relation to the processing by processor 220.

The processing may include stage 621 of processing the signals to detect any predefined condition related to one or more of the following physiological parameters: blood pressure, oxygen saturation, blood glucose, lung functions, body temperature, respiratory system parameters, arrhythmia (including but not limited to Atrial fibrillation, weight and the like.

The processing may include at least one of the following: (i) determining when a value of physiological parameter exceeded a first threshold for at least a first minimum duration (wherein the exceeding heart rate may be either higher or lower than the first threshold, where applicable, as discussed above), (ii) determining when a value of the physiological parameter exceeded the second threshold for at least a second minimum duration, (iii) detecting when a value of the physiological parameter exceeded a third threshold or any additional threshold, (iv) triggering a first monitoring stated if the value of the physiological parameter exceeds the first threshold for a first minimum duration, and triggering a second monitoring state if the value of the physiological parameter exceeds the second threshold for a second minimum duration, wherein the triggering of the second monitoring state involves ceasing the first monitoring state, wherein timing information pertaining to the at least one first time period is gathered in the first monitoring state, and timing information pertaining to the at least one second time period is gathered in the second monitoring state. The same applied to more than two monitoring states.

Method 600 further includes stage 630 of providing monitoring results in response to a result of the processing, wherein the monitoring results include information indicative of: (a) the values of the physiological parameter during the monitoring period; (b) at least one first time period in which the value of the physiological parameter exceeded a first threshold; and (c) at least one second time period in which the value of the physiological parameter exceeded both the first threshold and a second threshold. The same applied to more than two thresholds.

Referring to the examples set forth in the previous drawings, the providing of the monitoring results may be carried out by an output interface such as output interfaces 230, 230(1), 230(2), and/or 230(3).

It is noted that the providing may be carried out during the monitoring period, and/or after it is over, according to various embodiments of the invention, e.g. as discussed above in relation to the providing by output interface 230.

Method 600 may further include stage 640 of issuing an alert when at least one of the first and the second thresholds was exceeded for a predetermined minimum duration.

The issuing may include stage 641 of wirelessly transmitting the alert to a remote control center over a cellular telephony network Method 600 may further include stage 650 of storing a physiological parameter history of values of a physiological parameter detected during the monitoring period, wherein the storing may include stage 551 of replacing stored information with newer detected information, wherein the replacing of stage 551 is responsive to priority levels that are associated with the first and the second thresholds.

Method 600 may further include stage 660 of receiving wireless instructions over a wireless network connection, and modifying at least one of the first and the second thresholds in response to the wireless instructions.

According to an embodiment of the invention, the providing of the monitoring results may further include providing the monitoring results that further includes information indicative of at least one exceeding time period in which the physiological parameter exceeded the first threshold, the second threshold, and at least one additional threshold.

According to an embodiment of the invention, the issuing may further include issuing an alert when at least one of the at least one additional thresholds was exceeded for a predetermined minimum duration.

It is noted that the invention may implement three, four, five, six, or more thresholds. According to some embodiments of the invention, some of the thresholds may not be predetermined, and may be determined (or updated) in response to dynamically determined results. For example—if the first threshold was exceeded for a prolonged period, the second threshold may be updated to a lower or higher value than was set before.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for monitoring a heart of a patient, the method comprising: receiving, by a physiological data input interface and from one or more sensors, signals indicative of cardiac activity of the patient during a monitoring period; processing, by a processor, the signals and; providing by the processor, monitoring results in response to a result of the processing; wherein the monitoring results comprise information indicative of: (a) a heart rate of the patient during the monitoring period; (b) at least one first time period in which the heart rate of the patient exceeds a first threshold; and (c) at least one second time period in which the heart rate of the patient exceeds both the first threshold and a second threshold;
   wherein the providing, by the processor, of the monitoring results comprises: providing a first bradycardia indication if the heart rate of the patient was lower than the first threshold for a first bradycardia indicative duration, and providing a second bradycardia indication if the heart rate of the patient was lower than the second threshold that is lower than the first threshold;
   wherein the processing, by the processor, further comprises processing the signals to detect heart pauses,
   wherein the providing of the monitoring results further comprises providing a pause indication, wherein the pause indication that is indicative of at least one heart pause and which is distinct from the first and second bradycardia indications.

2. The method according to claim 1, wherein the processing, by the processor, further comprises processing the signals to detect atrial fibrillation, wherein the providing of the monitoring results further comprises providing information indicative of atrial fibrillation of the heart of the patient during the monitoring period.

3. A method for monitoring a heart of a patient, the method comprising: receiving, by a physiological data input interface and from one or more sensors, signals indicative of cardiac activity of the patient during a monitoring period; processing, by a processor, the signals and; providing by the processor, monitoring results in response to a result of the processing; wherein the monitoring results comprise information indicative of: (a) a heart rate of the patient during the monitoring period; (b) at least one first time period in which the heart rate of the patient exceeds a first threshold; and (c) at least one second time period in which the heart rate of the patient exceeds both the first threshold and a second threshold;
   wherein the processing, by the processor, comprises determining when the heart rate of the patient exceeded the first threshold for at least a first minimum duration, wherein the providing comprises providing the monitoring results that comprise information pertaining to first time periods that are longer than the first minimum duration.

4. The method according to claim 3, wherein the processing, by the processor, further comprises determining when the heart rate of the patient exceeded the second threshold for at least a second minimum duration, wherein the providing comprises providing the monitoring results that comprise information pertaining to second time periods that are longer than the second minimum duration.

5. The method according to claim 3, further comprising issuing, by an output interface, an alert when the first threshold was exceeded for at least the first minimum duration.

6. The method according to claim 5, wherein the issuing by the output interface, of the alert comprises wirelessly transmitting the alert to a remote control center over a cellular telephony network.

7. A method for monitoring a heart of a patient, the method comprising: receiving, by a physiological data input interface and from one or more sensors, signals indicative of cardiac activity of the patient during a monitoring period; processing, by a processor, the signals and; providing by the processor, monitoring results in response to a result of the processing; wherein the monitoring results comprise information indicative of: (a) a heart rate of the patient during the monitoring period; (b) at least one first time period in which the heart rate of the patient exceeds a first threshold; and (c) at least one second time period in which the heart rate of the patient exceeds both the first threshold and a second threshold; wherein the providing, by the processor, of the monitoring results comprises providing monitoring summary of the monitoring period, wherein the monitoring summary comprises: a first time summation responsive to times in which the heart rate of the patient exceeded the first threshold for periods longer than a first minimum duration, and a second time summation responsive to times in which the heart rate of the patient exceeded the second threshold for periods longer than a second minimum duration.

8. The method according to claim 7, further comprising storing a heart rate history of heart rates detected during the monitoring period, wherein the storing comprises replacing stored information with newer detected information, wherein the replacing is responsive to priority levels that are associated with the first and the second thresholds.

9. The method according to claim 7, further comprising receiving wireless instructions over a wireless network connection, and modifying at least one of the first and the second thresholds in response to the wireless instructions.

10. The method according to claim 7, wherein the providing, by the processor, of the monitoring results further comprises providing results that are responsive to information gathered by at least one additional sensor that is selected from an oxygen saturation sensor, a mechanical sensor, and an environmental sensor.

11. A method for monitoring a heart of a patient, the method comprising: receiving, by a physiological data input interface and from one or more sensors, signals indicative of cardiac activity of the patient during a monitoring period; processing, by a processor, the signals and providing by the processor, monitoring results in response to a result of the processing; wherein the monitoring results comprise information indicative of: (a) a heart rate of the patient during the monitoring period; (b) at least one first time period in which the heart rate of the patient exceeds a first threshold; and (c) at least one second time period in which the heart rate of the patient exceeds both the first threshold and a second threshold;
wherein the processing, by the processor, comprises: triggering a first monitoring state if the heart rate of the patient exceeds the first threshold for a first minimum duration, and triggering a second monitoring state if the heart rate of the patient exceeds the second threshold for a second minimum duration, wherein the triggering of the second monitoring state involves ceasing the first monitoring state, wherein timing information pertaining to the at least one first time period is gathered in the first monitoring state, and timing information pertaining to the at least one second time period is gathered in the second monitoring state.

12. A method for monitoring a heart of a patient, the method comprising: receiving, by a physiological data input interface and from one or more sensors, signals indicative of cardiac activity of the patient during a monitoring period; processing, by a processor, the signals and providing by the processor, monitoring results in response to a result of the processing; wherein the monitoring results comprise information indicative of: (a) a heart rate of the patient during the monitoring period; (b) at least one first time period in which the heart rate of the patient exceeds a first threshold; and (c) at least one second time period in which the heart rate of the patient exceeds both the first threshold and a second threshold;
wherein the providing, by the processor, of the monitoring results further comprises providing the monitoring results that further comprise information indicative of at least one exceeding time period in which the heart rate of the patient exceeded the first threshold, the second threshold, and at least one additional threshold.

13. The method according to claim 12, wherein the providing by the processor, of the monitoring results comprises: providing a first tachycardia indication if the heart rate of the patient was higher than the first threshold for a first tachycardia indicative duration, and providing a second tachycardia indication if the heart rate of the patient was higher than the second threshold, wherein the second threshold is higher than the first threshold.

14. The method according to claim 12, wherein the providing, by the processor, of the monitoring results comprises: providing a first bradycardia indication if the heart rate of the patient was lower than the first threshold for a first bradycardia indicative duration, and providing a second bradycardia indication if the heart rate of the patient was lower than the second threshold that is lower than the first threshold.

15. The method according to claim 12, wherein the providing, by the processor, of the monitoring results comprises: providing a first tachycardia indication if the heart rate of the patient was higher than a first tachycardia threshold for a first tachycardia indicative duration; providing a second tachycardia indication if the heart rate of the patient was higher than a second tachycardia threshold that is higher than the first tachycardia threshold; providing a first bradycardia indication if the heart rate of the patient was lower than a first bradycardia threshold for a first bradycardia indicative duration, and providing a second bradycardia indication if the heart rate of the patient was lower than a second bradycardia threshold that is lower than the first threshold.

16. The method according to claim 12 comprising providing the monitoring results in a medical report form, wherein the medical report form comprises: (a) information indicative of the heart rate of the patient during the monitoring period; (b) information indicative of the at least one first time period within the monitoring period in which the heart rate of the patient exceeded the first threshold; and (c) information indicative of the at least one second time period in which the heart rate of the patient exceeded both the first threshold and the second threshold.

17. The method according to claim 16 wherein the medical report form comprising information indicative of cardiac events, which is responsive to the exceeding of at least one of the first and the second thresholds.

* * * * *